United States Patent
Di Carlo et al.

(10) Patent No.: US 9,333,510 B2
(45) Date of Patent: May 10, 2016

(54) DEVICES AND METHODS FOR SHAPE-BASED PARTICLE SEPARATION

(71) Applicant: THE REGENTS OF THE UNIVERSITY OF CALIFORNIA, Oakland, CA (US)

(72) Inventors: Dino Di Carlo, Los Angeles, CA (US); Mahdokht Masaeli, Los Angeles, CA (US); Elodie Sollier, Gagny (FR)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/346,290

(22) PCT Filed: Sep. 27, 2012

(86) PCT No.: PCT/US2012/057631
§ 371 (c)(1),
(2) Date: Mar. 20, 2014

(87) PCT Pub. No.: WO2013/089883
PCT Pub. Date: Jun. 20, 2013

(65) Prior Publication Data
US 2014/0224710 A1    Aug. 14, 2014

Related U.S. Application Data

(60) Provisional application No. 61/541,934, filed on Sep. 30, 2011, provisional application No. 61/606,287, filed on Mar. 2, 2012.

(51) Int. Cl.
*B03B 5/48* (2006.01)
*G01N 1/40* (2006.01)
(Continued)

(52) U.S. Cl.
CPC ............. *B03B 5/48* (2013.01); *B01L 3/502746* (2013.01); *B01L 3/502761* (2013.01);
(Continued)

(58) Field of Classification Search
CPC ... G01N 15/02; G01N 15/05; G01N 15/0255; G01N 2015/0288; G01N 2015/0294; G01N 2015/1081; G01N 2015/1087; G01N 2015/1093; G01N 2015/0065; G01N 35/08; G01N 1/4077; B01L 2200/0652; B01L 3/5027; B01L 3/502715; B01L 3/502746; B01L 3/502753; B01L 3/502776; B01L 2300/0864; B03B 5/48
USPC .......................................... 209/132, 155, 208
See application file for complete search history.

(56) References Cited

U.S. PATENT DOCUMENTS 7,735,652 B2 * 6/2010 Inglis et al. ................... 209/155
8,590,710 B2 * 11/2013 Sim et al. ...................... 209/644
(Continued)

FOREIGN PATENT DOCUMENTS

WO    WO 2011/109762    9/2011

OTHER PUBLICATIONS

Beech, Jason P. et al., Shape-based particle sorting—A new paradigm in microfluidics, Proc. Micro Total Analysis Systems, Jeju, Korea, 800-802 (2009).
(Continued)

*Primary Examiner* — Michael McCullough
(74) *Attorney, Agent, or Firm* — Vista IP Law Group LLP

(57) ABSTRACT

A particle sorting system includes an inlet and an inertial focusing microchannel disposed in a substrate and having a downstream expanding region at a distal end, wherein the inlet is connected to an upstream end of the microchannel. A source of different shaped particles is connected to the inlet, wherein the source of different shaped particles are configured for continuous introduction into the inlet. A plurality of outlets is connected to the microchannel at the downstream expanding region. Fluidic resistors are located in the respective outlets. Different resistances may be used in the outlets to capture enriched fractions of particles having particular particle shape(s).

14 Claims, 12 Drawing Sheets

(51) Int. Cl.
G01N 35/08 (2006.01)
G01N 15/02 (2006.01)
B01L 3/00 (2006.01)
G01N 15/00 (2006.01)

(52) U.S. Cl.
CPC ............. *G01N 1/4077* (2013.01); *G01N 15/02* (2013.01); *G01N 35/08* (2013.01); *B01L 2200/0636* (2013.01); *B01L 2200/0652* (2013.01); *B01L 2300/088* (2013.01); *B01L 2300/0816* (2013.01); *B01L 2300/0864* (2013.01); *B01L 2400/0487* (2013.01); *G01N 2015/0065* (2013.01); *G01N 2015/0288* (2013.01); *G01N 2015/0294* (2013.01)

(56) References Cited

U.S. PATENT DOCUMENTS

2009/0014360 A1    1/2009  Toner et al.
2011/0017645 A1*   1/2011  Hongo et al. ................. 209/157
2012/0315690 A1*  12/2012  Di Carlo et al. ........... 435/287.1

OTHER PUBLICATIONS

Champion, Julie A. et al., Role of target geometry in phagocytosis, Proc. Natl. Acad. Sci. USA 103(13):4930-4934 (2006).
Choi, Sungyoung et al., Continuous hydrophoretic separation and sizing of microparticles using slanted obstacles in a microchannel, Lab Chip, Jul.; 7(7): 890-97 (2007).
Di Carlo, Dino et al., Continuous inertial focusing, ordering, and separation of particles in microchannels. PNAS, 104, 48, 18892-18897 (2007).
Huang, Lotien Richard et al., Continuous Particle Separation Through Deterministic Lateral Displacement, Science, vol. 304 No. 5673 pp. 987-990 (May 2004).
Ookawara, Shinichi et al., K. Feasibility Study on Concentrator of Slurry and Classification of Contained Particles by Micro-Channel, Chem. Eng. J., v.101, 171-178 (2004).
Sharma, Vivek et al., Shape separation of gold nanorods using centrifugation. PNAS, 106, 13, 4981-4985 (2009).
Sugaya, Sari et al., Observation of nonspherical particle behaviors for continuous shape-based separation using hydrodynamic filtration, Biomicrofluidics, 5, 024103 (2011).
Takagi, Junya et al., Continuous particle separation in a microchannel having asymmetrically arranged multiple branches, Lab Chip, Jul.; 5(7) 778-84 (2005).
Valero, Ana et al., Tracking and synchronization of the yeast cell cycle using dielectrophoretic opacity, Lab Chip, 11, 1754-1760 (2011).
Yamada, Masumi et al., Hydrodynamic filtration for on-chip particle concentration and classification utilizing microfluidics, Lab Chip, Nov.; 5(11): 1233-39 (2005).
Bhagat, Alis Asgar S., et al., Pinched flow coupled shear-modulated inertial microfluidics for high-throughput rare blood cell separation, Lab Chip, 2011, 11, 1870-1878.
Hur, Soojung Claire, et al., Deformability-based cell classification and enrichment using inertial microfluidics, Lab Chip, 2011, 11, 912-920.
Kuntaegowdanahalli, Sathyakumar S., et al., Inertial microfluidics for continuous particle separation in spiral microchannels, Lab Chip, 2009, 9, 2973-2980.
PCT International Search Report for PCT/US2012/057631, Applicant: The Regents of the University of California, Form PCT/ISA/210 and 220, dated Jul. 11, 2013 (5pages).
PCT Written Opinion of the International Search Authority for PCT/US2012/057631, Applicant: The Regents of the University of California,, Form PCT/ISA/237, dated Jul. 11, 2013 (5pages).
PCT International Preliminary Report on Patentability (Chapter I of the Patent Cooperation Treaty) for PCT/US2012/057631, Applicant: The Regents of the University of California, Form PCT/IB/326 and 373, dated Apr. 10, 2014 (7pages).
Chinese Patent Office Communication dated Apr. 1, 2015 in Chinese Patent Application No. 2012800594140 (15pages).
European Patent Office Communication dated May 6, 2015 in European Patent Application No. 12856833.4-1553 (8pages).
Hur, Soojung et al., Inertial Focusing of Non-Spherical Microparticles, Applied Physics Letters, American Institute of Physics, US, vol. 99, No. 4, Jul. 29, 2011, pp. 44101-44101, XP012141610, ISSN: 003-6951, DOI: 10.1063/1.3608115.
Takagi, Junya et al., Continuous Particle Separation in a Microchannel Having Asymmetrically Arranged Multiple Branches, Lab on a chip, vol. 5, No. 7, Jan. 1, 2005, p. 778, XP055022575, ISSN: 1473-0197, DOI: 10.1039/b501885d.

* cited by examiner

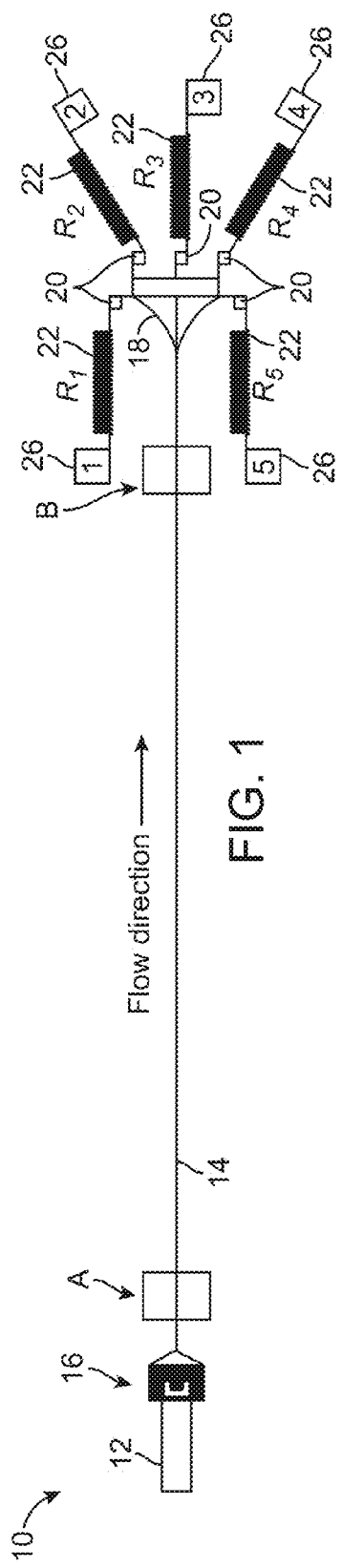

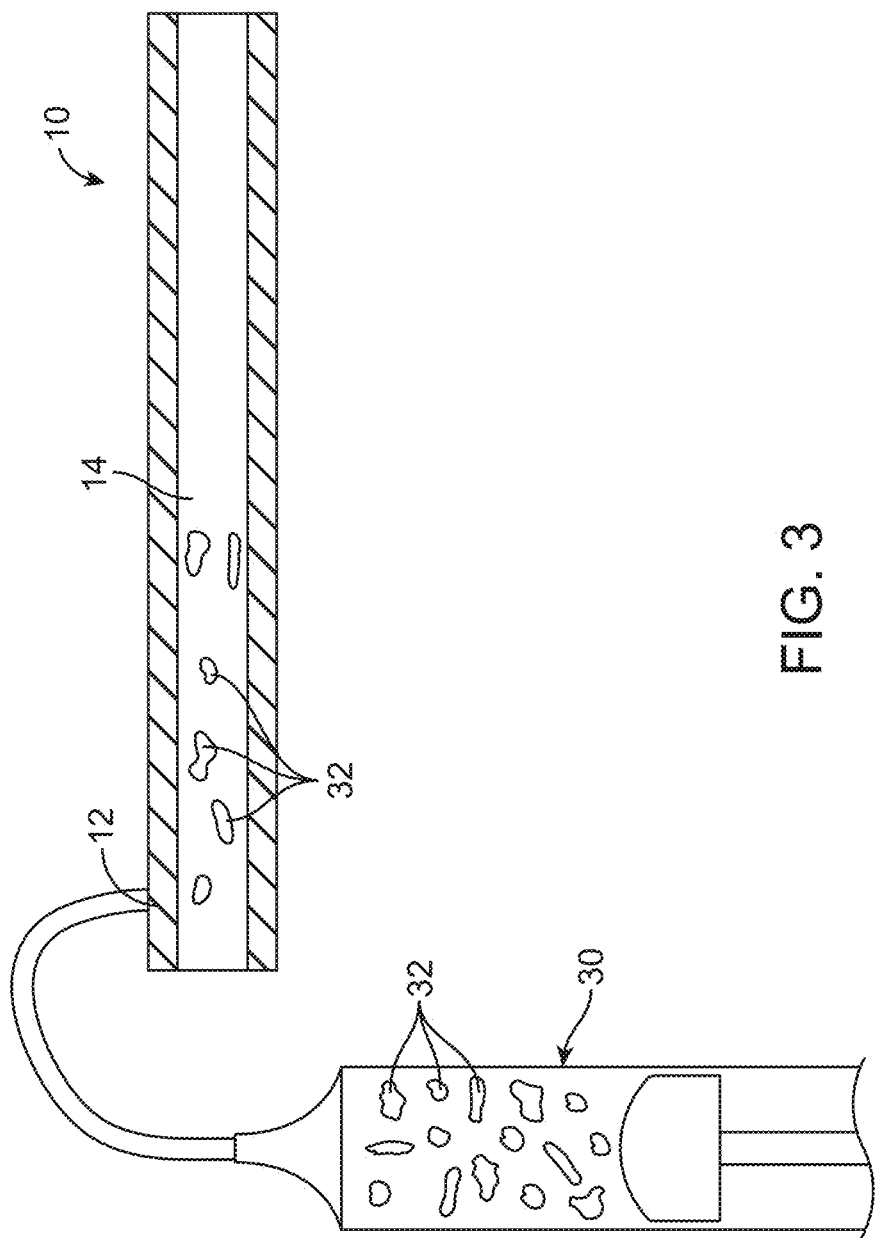

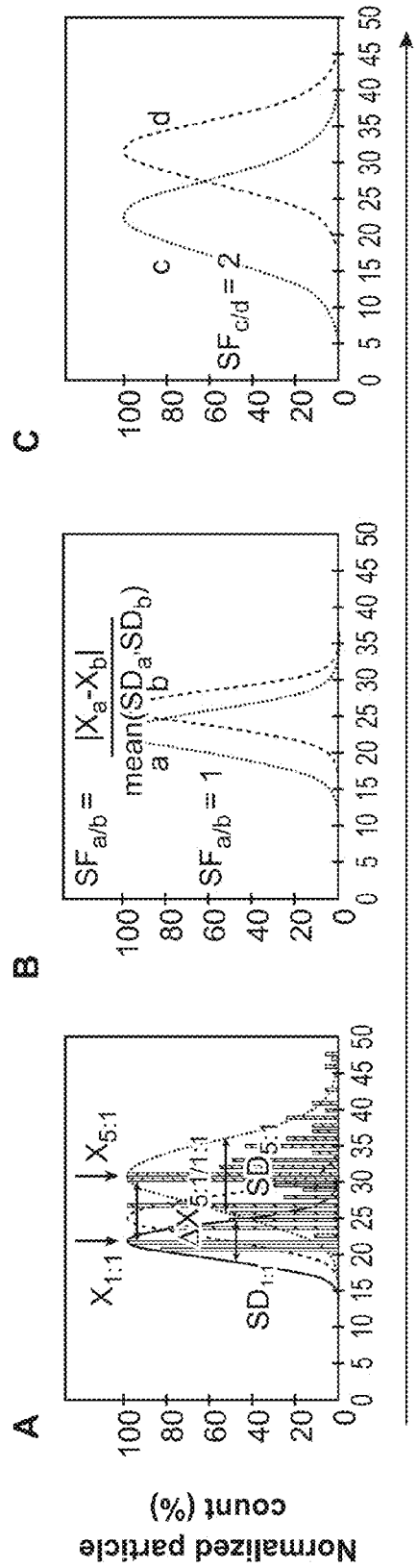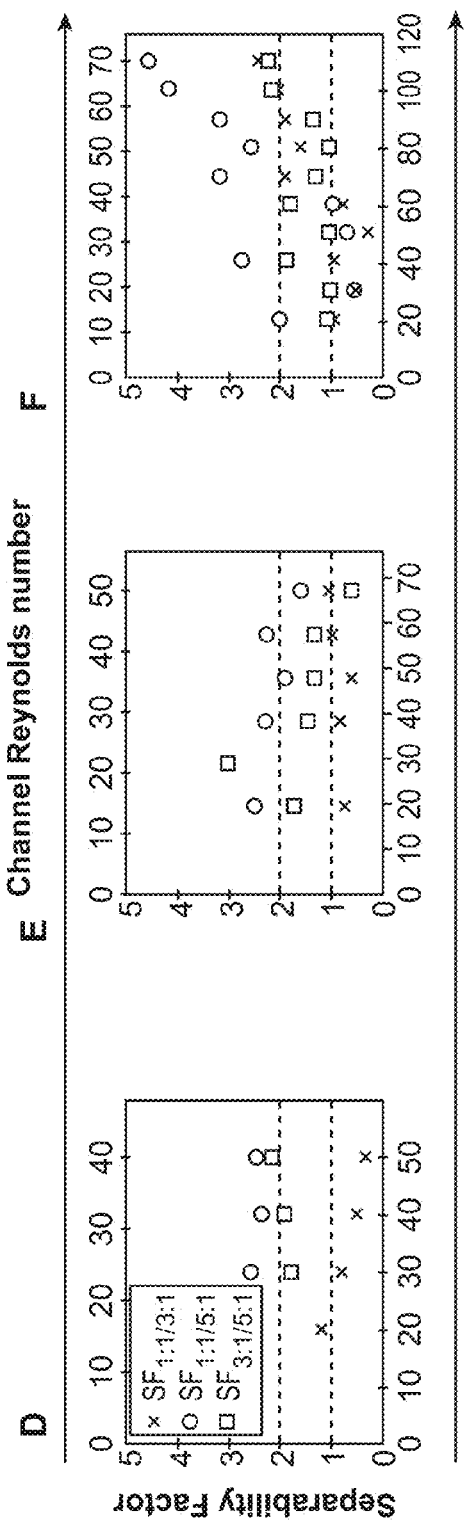
FIG. 6A
FIG. 6B

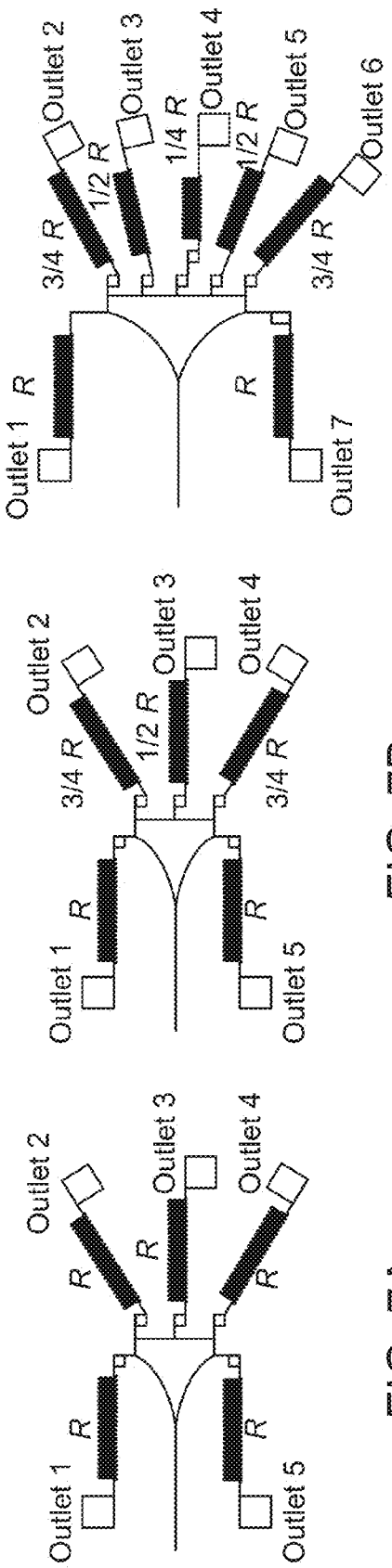
FIG. 7A
FIG. 7B
FIG. 7C
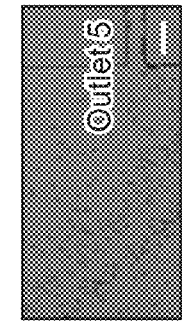
FIG. 7D
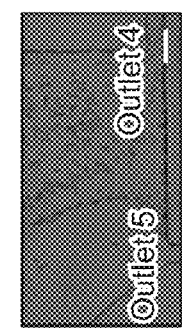
FIG. 7E
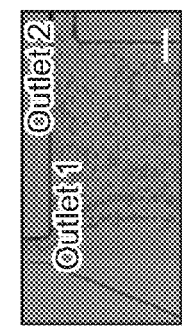
FIG. 7F

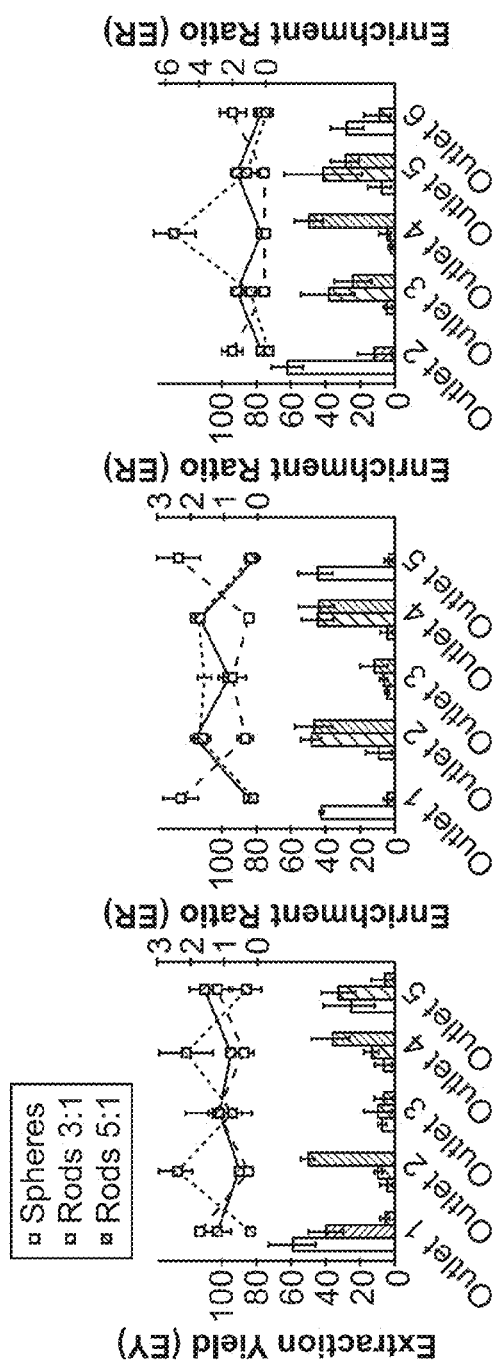
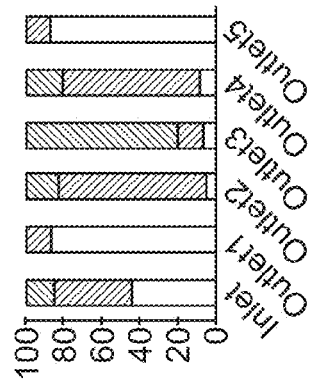
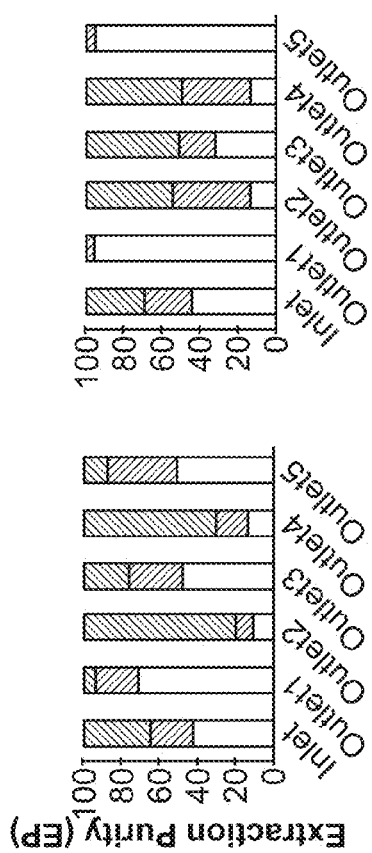
FIG. 7G  FIG. 7H  FIG. 7I
FIG. 7J  FIG. 7K  FIG. 7L

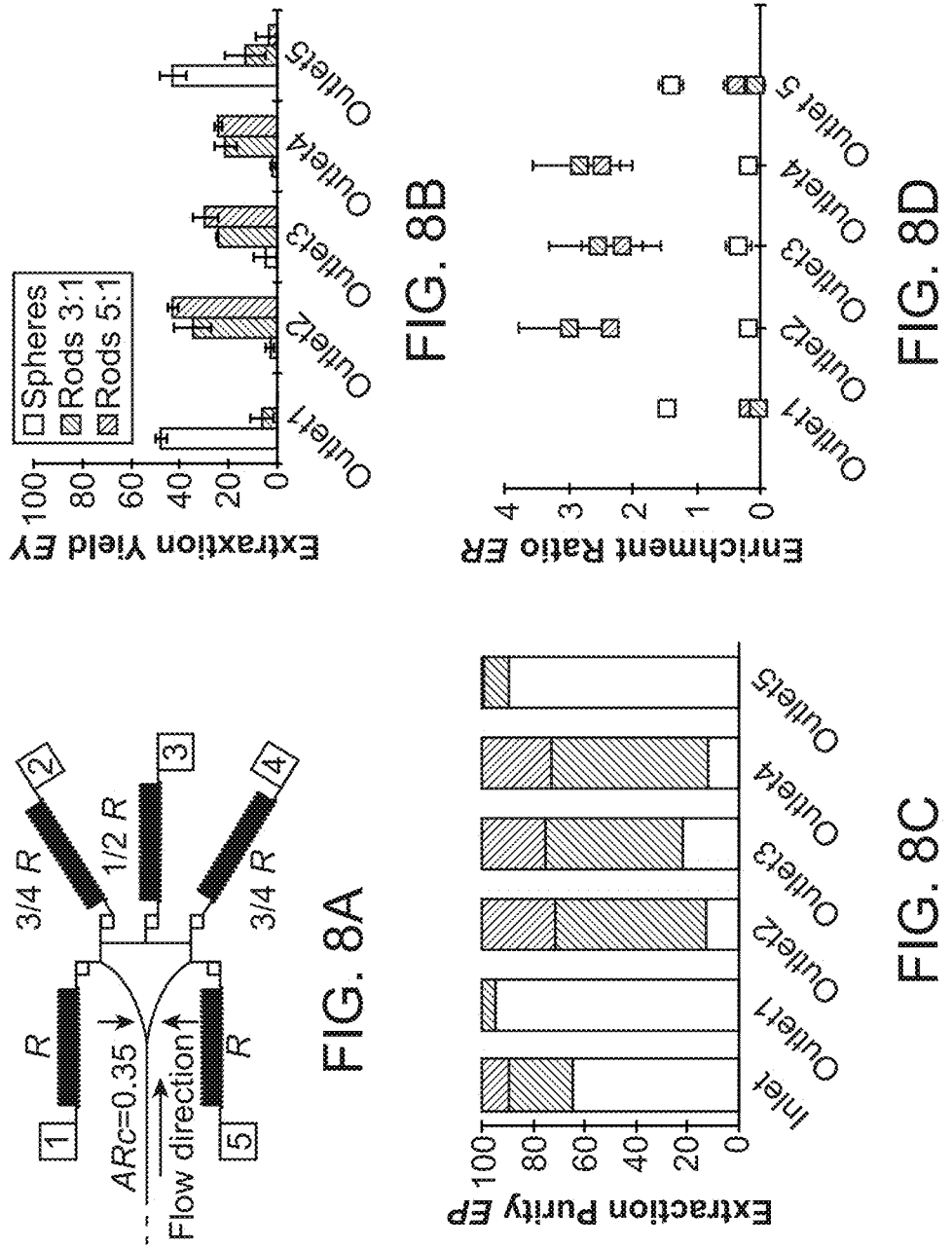

DEVICES AND METHODS FOR SHAPE-BASED PARTICLE SEPARATION

RELATED APPLICATIONS

This Application is a U.S. National Stage filing under 35 U.S.C. §371 of International Application No. PCT/US2012/057631, filed Sep. 27, 2012, which claims priority to U.S. Provisional Patent Application No. 61/541,934, filed on Sep. 30, 2011 and U.S. Provisional Patent Application No. 61/606,287, filed on Mar. 2, 2012. The contents of the aforementioned applications are hereby incorporated herein by reference in their entirely. Priority to the aforementioned applications are hereby expressly claimed in accordance with 35 U.S.C. §§119, 120, 365 and 371 and any other applicable statutes.

STATEMENT REGARDING FEDERALLY SPONSORED RESEARCH OR DEVELOPMENT

This invention was made with Government support under 0930501, awarded by the National Science Foundation (EDISON). The Government has certain rights in the invention

FIELD OF THE INVENTION

The field of the invention generally relates to microfluidic devices used for separation and sorting applications. More particularly, the field of the invention relates to the microfluidic devices used to separate and sort particles based on their respective shapes.

BACKGROUND

Various attempts have been made using microfluidics for the continuous separation of cells or microparticles. Some of the approaches combine microfluidics with an externally applied force field. For example, electrical, magnetic, optical, and acoustic-based forces have been attempted to separate particles. Still other approaches are based on the passive hydrodynamics created in microchannels. For example, various filters (e.g., weir-type, cross-flow type) and membranes have been proposed that operate based on size-exclusion principles. For example, Takagi et al. have developed a continuous particle separation technique that uses a microchannel having asymmetrically arranged multiple branch channels. See Takagi et al., Continuous particle separation in a microchannel having asymmetrically arranged multiple branches, Lab Chip, July; 5(7) 778-84 (2005). This method improves the separation scheme of pinched flow fractionation (PFF), which uses laminar flow within a microchannel.

Yamada et al. have proposed a microfluidic device for the continuous concentration and classification of particles using hydrodynamic filtration (HDF). This method uses various side channels to align particles along the wall of a microfluidic channel. Additional downstream selection channels are used to selectively extract different particles from the main channel. See Yamada et al., Hydrodynamic filtration for on-chip particle concentration and classification utilizing microfluidics, Lab Chip, November; 5(11): 1233-39 (2005). Choi et al. have developed a microfluidic separation and sizing technique for microparticles that uses hydrophoresis, the movement of suspended particles under the influence of a microstructure-induced pressure field. By exploiting slanted obstacles in a microchannel, one can generate a lateral pressure gradient so that microparticles can be deflected and arranged along the lateral flows induced by the gradient. See Choi et al., Continuous hydrophoretic separation and sizing of microparticles using slanted obstacles in a microchannel, Lab Chip, July; 7(7): 890-97 (2007).

Huang et al. have proposed a continuous particle separation method through deterministic lateral displacement (DLD). See Huang et al., Continuous Particle Separation Through Deterministic Lateral Displacement, Science, Vol. 304 No. 5673 pp. 987-990 (May 2004). This technique makes use of the asymmetric bifurcation of laminar flow around obstacles. A particle chooses its path deterministically on the basis of its size. Other methods are based on centrifugal separation. For instance, Ookawara et al. reported on the use of 200 µm×170 µm microchannels with semicircular radius of 2 mm for centrifugal separation where slurry particles are directed into one arm of a bifurcation channel. See Ookawara et al., K. Feasibility Study on Concentrator of Slurry and Classification of Contained Particles by Micro-Channel, Chem. Eng. J., v. 101, 171-178 (2004). More recently, Di Carlo et al. have developed an inertial focusing, ordering, and separation technique that orders particles in a controlled manner within a microfluidic channel. See Di Carlo et al., Continuous inertial focusing, ordering, and separation of particles in microchannels. PNAS, 104, 48, 18892-18897 (2007).

Shape, however, has rarely been considered in most of these integrated separation techniques, generally using the particle size, deformability, density, electric or magnetic characteristics or even its surface molecules to separate the particles while assuming cells and particles are spherical. Centrifugation, which is the macro-scale conventional technique for micro-particle separation, has been lately considered for shape-separation of spheres and rods. See Sharma et al., Shape separation of gold nanorods using centrifugation. PNAS, 106, 13, 4981-4985 (2009). Only recently, hydrodynamic filtration (HDF), deterministic lateral displacement (DLD) and dielectrophoresis (DEP) have begun considering shape as a criterion of separation in microsystems. Beech et al. first introduced the shape-based sorting with DLD technique, showing that non-spherical particles can be oriented in DLD devices via controlling device depth resulting in different effective dimensions to the pillars network. See Beech et al., Shape-based particle sorting—A new paradigm in microfluidics, Proc. Micro Total Analysis Systems, Jeju, Korea, 800-802 (2009). More recently, Sugaya et al. investigated the applicability of HDF for shape-based separation and demonstrated a difference in the separation behaviors of spherical and nonspherical particles at a branch point and used this technique for sorting budding/single cells from a yeast cell mixture. See Sugaya et al., Observation of non-spherical particle behaviors for continuous shape-based separation using hydrodynamic filtration, Biomicrofluidics, 5, 024103 (2011). Similarly, Valero et al. validated the shape-based sorting of yeast by balancing opposing DEP forces at multiple frequencies. See Valero et al., Tracking and synchronization of the yeast cell cycle using dielectrophoretic opacity, Lab Chip, 11, 1754-1760 (2011).

HDF and DLD are continuous and efficient techniques but both require low flow rates (2-3 µL/min and 60 mL/min, respectively) and high dilution factors, consequently offering a low throughput. These techniques also require accurately defined fabrication processes and complex designs, since the features that are necessary to guarantee the separation (pillar networks for DLD, highly-parallelized channels for HDF) have to be precisely designed (<1 µm-resolution). On the other hand, DEP requires the integration of active elements and a precise and reproducible control of the buffer conductivity between each experiment, which also complicates its integration in a whole-integrated microsystem. DEP based solutions require additional integration of active elements and a precise and reproducible control of the buffer conductivity between runs which makes DEP-based devices complicated and costly.

SUMMARY

In one aspect of the invention, a particle sorting system includes an inlet and an inertial focusing microchannel disposed in a substrate and having a downstream expanding region at a distal end, wherein the inlet is connected to an upstream end of the microchannel. A source of different shaped particles is connected to the inlet, wherein the source of different shaped particles is configured for continuous introduction into the inlet. A plurality of outlets is connected to the microchannel at the downstream expanding region. Fluidic resistors are located in the respective outlets. Different resistances may be used in the outlets to capture enriched fractions of particles having particular particle shape(s).

A method of sorting different shaped particles suspended in a sample fluid includes the operations of flowing the sample fluid containing different shaped particles suspended therein through a particle sorting system. The system includes an inertial focusing microchannel disposed in a substrate and having a downstream expanding region at a distal end and a plurality of outlets coupled to the downstream expanding region. A plurality of fluidic resistors are located respective outlets. In the method, fluid is collected in each of the plurality of outlets, wherein at least one of the outlets contains fluid enriched in at least one shape of particle compared to the sample fluid.

BRIEF DESCRIPTION OF THE DRAWINGS

FIG. 1 illustrates a particle sorting system or device according to one embodiment.

FIG. 2A illustrates a magnified view of a downstream expanding region that terminates into three separate outlets. Two outlets have identical fluidic resistors while the central fluidic resistor has less resistance.

FIG. 3 illustrates a source of particles coupled to the inlet of a particle sorting system.

FIG. 6A illustrates in panel image A a representative Gaussian fit of normalized particle count (%) as a function of $X_{eq}$ for spherical and 1:5 rod particles. Image panel B shows a Separability Factor of 1. Image panel C shows a Separability Factor of 2.

FIG. 6B illustrates the Separability Factor obtained for the 25 μm wide channel (image D), the 30 μm wide channel (image E), and the 35 μm wide channel (image F) at various flow rates.

FIGS. 7A-7C illustrates three different configurations of a particle sorting system that were tested.

FIG. 7D illustrates a micrographic image of the area between outlets 1 and 2.

FIG. 7E illustrates a micrographic image of the area between outlets 4 and 5.

FIG. 7F illustrates a micrographic image of the area around outlet 5.

FIG. 7G illustrates the EY and ER of various particles at each outlet of the device of FIG. 7A.

FIG. 7H illustrates the EY and ER of various particles at each outlet of the device of FIG. 7B.

FIG. 7I illustrates the EY and ER of various particles at each outlet of the device of FIG. 7C.

FIG. 7J illustrates the EP of various particles at each outlet of the device of FIG. 7A.

FIG. 7K illustrates the EP of various particles at each outlet of the device of FIG. 7B.

FIG. 7L illustrates the EP of various particles at each outlet of the device of FIG. 7C.

FIG. 8A illustrates a particle sorting system according to another embodiment.

FIG. 8B illustrates a graph of EY for each of the five outlets of the device of FIG. 8A.

FIG. 8C illustrates a graph of the EP for each of the five outlets of the device of FIG. 8A.

FIG. 8D illustrates a graph of the ER for each of the five outlets of the device of FIG. 8A.

DETAILED DESCRIPTION OF THE ILLUSTRATED EMBODIMENTS

Figure 2B:
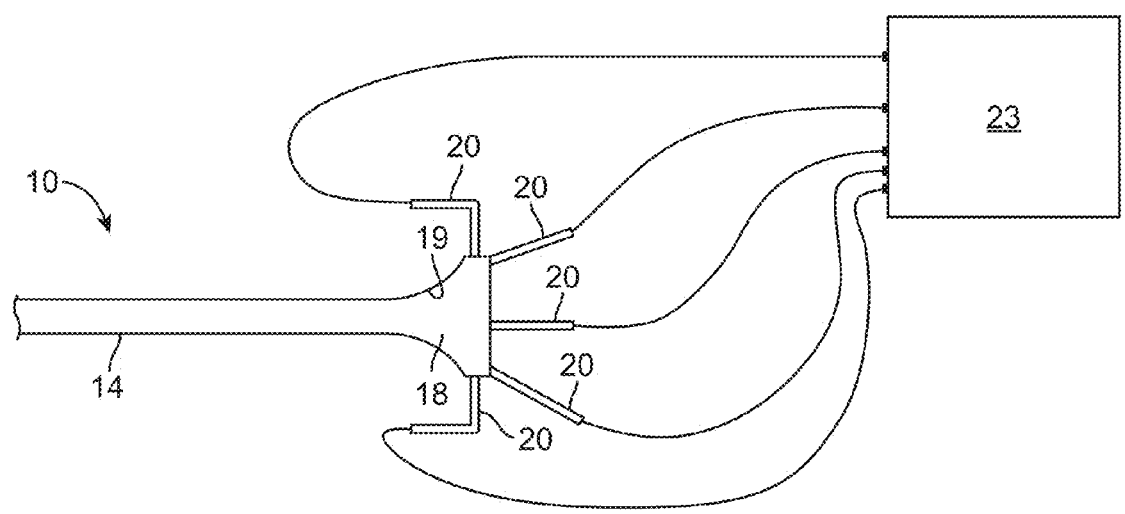
FIG. 2B illustrates an alternative embodiment of a particle sorting device that uses a pressure controller to adjust the fluidic resistances of the plurality of outlets.

FIG. 1 illustrates a particle sorting system 10 according to one embodiment. The particle sorting system 10 may be formed in any number of materials suitable for microfluidic applications. For example, the features of the particle sorting system 10 can be formed in Polydimethylsiloxane (PDMS) which is then bonded to a planar substrate such as glass or plastic using a common PDMS replica molding process. Briefly, standard lithographic techniques were used to produce a mold from a silicon master spin-coated with SU-8 photoresist. PDMS chips were produced from this mold using Sylgard 184 Elastomer Kit (Dow Corning Corporation) and a cross-linker to polymer ratio of 1:10. To enclose the channels, PDMS and glass were both activated by air plasma (Plasma Cleaner, Harrick Plasma, 500 mTorr, 30 sec) before being bonded together.

Alternatively, the features of the particle sorting system 10 may be directly formed on a substrate such as silicon or even a polymer such as plastic using lithographic or other similar techniques known to produce microfluidic devices. An advantage of the particle sorting system 10 is that it can be fabricated with standard microfluidic fabrication techniques which decreases the time and cost of fabrication. Moreover, there is no need for any external setup to induce particle separation as opposed to active methods. Separation relies on device geometry and the presence of the fluid as a driving force. Unlike DLD and HDF based devices which require low flow rates, the particle sorting system 10 described herein can be used with relatively high flow rates, which means the device can achieve high throughput.

As used herein, "particle" refers to a small object dimensioned on the micrometer or smaller scale. Particles can include both live and non-living objects. Examples of particles include cells, bacteria, viruses, and the like. Particles may include organelles or sub-components of larger biological constituents. Particles can also include inanimate objects like beads or the like. Particles may be bonded or conjugated with other species. Particles include both single or separate particles as well as agglomerations of other smaller objects.

The particle sorting system includes an inlet 12 that is connected to an upstream end of an inertial focusing microchannel 14. As seen in FIG. 1, there is an optional filter 16 for capturing debris or other large particles of interest. The optional filter 16 may be formed on one or more protuberances, posts, or the like that prevent the passage of large or bulky particles into the inertial focusing microchannel 14. The inertial focusing microchannel 14 may have a length of several centimeters (e.g., 4 cm) and a rectangular cross-section. For example, the inertial focusing microchannel 14 may have a height of around 50 µm and a width within the range of around 25-35 µm although other dimensions outside this range are contemplated.

The inertial focusing microchannel 14 terminates at a downstream end in a downstream expanding region 18. The downstream expanding region 18 preferably gradually extends laterally as one moves along the direction of flow (direction of arrow A in FIG. 2A). In this regard, the contours of the edges of the channel 19 that define the downstream expanding region 18 as seen in FIG. 2A are curved or parabolic as opposed to a straight-angled expansion chamber. Generally, a smooth-shaped transition from the inertial focusing microchannel 14 to the downstream expanding region 18 is preferred. For example, the walls defining the downstream expanding region 18 may progressively angle outward as one moves downstream in the direction of fluid flow. For example, the walls defining the downstream expanding region may progressively increase at an angle of 2° per 100 µm of movement in along the direction of fluid flow. As explained below, the downstream expanding region 18 maintains focused particles in the focusing streamlines while enhancing their lateral spacing (Xeq).

Still referring to FIG. 1, a plurality of outlets 20 are connected to the downstream expanding region 18. Each outlet 20 may be an outlet channel that opens at one end to the expanding region 18. Five (5) such outlets 20 are illustrated although more or less may be used. Each outlet 20 is shown including a fluidic resistor 22 which is graphically illustrated in FIG. 1. The fluidic resistor 22 may be formed from a structure or structures that restrict flow in the outlets 20. As one example, the flow restrictor is serpentine channel 24 having a plurality of turns such as that illustrated in FIG. 2A. For example, a fluidic resistor 22 may have twenty such turns for a total length of several centimeters. The number of turns may be used to adjust or tune the resistance of the fluidic resistor 22. For example, as seen in FIG. 2A, the middle fluidic resistor 22b has a resistance that is ½ that of the outer fluidic resistors 22a, 22c. As another example, the flow restrictor may be a channel with a reduced diameter or even a channel containing one or more structures configured to reduce flow therethrough. In another embodiment, the fluidic resistor 22 is not any sort of structure within the outlet 20 but is instead an applied or created pressure at the outlets 20.

For example, FIG. 2B illustrates an embodiment of a particle sorting system 10 that uses a pressure controller 23 that is coupled to the each outlet 20. The pressure controller 23 includes separate fluid lines 25 that are connected to each outlet 20. The pressure controller 23 is configured so that it can selectively apply different pressures to the various outlets 20. In this regard, the pressure controller 23 can tune the relative fluidic resistances of the outlets 20. In this embodiment, there is no need for serpentine channels to create the fluidic resistance. This functionality is transferred to the pressure controller 23. Further, the various fluidic resistances can be dynamically adjusted or tuned by the pressure controller 23. The particle sorting system 10 can thus be re-configured without having to make any physical changes to the particle sorting system 10.

Each fluidic resistor 22 may have the same or different fluidic resistance depending on the nature of the particles sorted in the particle sorting system 10. The fluidic resistor 22 in each outlet 20 may be specifically designed or "tuned" to capture enriched fractions of particles having particular particle shape(s). In the case where pressure is used as the fluidic resistor 22, relative flow through the various outlets 20 may be controlled by separately setting the pressure at the respective outlets 20 at defined rations. FIG. 1 illustrates five (5) fluidic resistors 22 ($R_1$, $R_2$, $R_3$, $R_4$, $R_5$) although more or less may be used. In addition, in some embodiments, there may be one or more outlets 20 that don't have any fluidic resistor 22 therein or applied thereto (in the case of pressure being the fluidic resistor 22). As seen in FIGS. 1 and 2, after each fluidic resistor 22, there is a respective outlet 26 (denoted 1, 2, 3, 4, and 5 in FIG. 1).

FIG. 3 illustrates a side view of a portion of the particle sorting system 10. The particle sorting system 10 is coupled via the inlet 12 to a source 30 of different shaped particles that is configured for continuous introduction into the inlet 12. FIG. 3 illustrates particles in the form of cells 32. The source 30 contains cells 32 that have a circular shape, a rod shape, and an irregular shape in this illustration although other particle types and shapes are contemplated. FIG. 3 illustrates a syringe as the source 30 of different shaped particles which can be used to continuously inject cells 32 into the particle sorting system 10. As used herein, continuous introduction means that particles are injected over an extended period of time as opposed to a single batch flow process. The syringe (or multiple syringes) may be coupled to a commonly used syringe pump to pump a fluid containing the cells 32 through the particle sorting system 10. The particles are carried by a carrier fluid (typically a liquid) which is also injected into the inlet 12. The particle sorting system 10 can work over a wide range of flow rates. As explained below, shape-based differences in focusing position were observed at flow rates within the range of 20 µL/min to 110 µL/min, however the upper limit was limited by the bonding strength of the device rather than the fluidic phenomena itself. Thus, flow rates outside this particular range are expected to also work.

While a syringe is illustrated in FIG. 3 as pumping the source 30 different shaped particles through the particle sorting system 10 other pressure or flow-based delivery devices used in connection with microfluidic devices may be used to continuously flow particles through the particle sorting system 10. In one aspect, fluid containing particles of different sizes or shapes are continuously pumped through the particle sorting system 10. The flow rate of particles through the particle sorting system 10 may be adjusted to effectuate different enrichment and collection of different shaped particles. Flow rates may be varied by the rate at which fluid is flowed through the system, channel geometries, and varied fluid resistance ratios. More broadly speaking, conditions may be changed to alter the Reynolds number.

To use the particle sorting system 10, the source 30 of different shaped particles is introduced continuously into the inlet 12 using a pressure or flow technique as discussed herein. The particle shapes may include any number of different shapes including circular, rod-like, oblong-shaped, elliptical-shaped, irregular-shaped particles. With reference to FIG. 1, at location A of the particle sorting system 10 different-shaped particles are randomly distributed throughout the inertial focusing microchannel 14. After flowing through along the majority of the inertial focusing microchannel 14 (e.g., around 4 cm at location B), the different shaped particles become focused at different locations or streams within the inertial focusing microchannel 14.

Each stream has a particular enriched quantity of particles of a particular shape. These streams are then given additional lateral separation by the downstream expanding region 18 where they are collected in the outlets 20. Different resistances in the fluidic resistors 22 may be used to collect different enriched fractions of particles. In addition, the dimensions of the inertial focusing microchannel 14 as well as the flow rate of particles through the particle sorting system 10 or Reynolds number may be adjusted to modify the number and position of separate streams created in the device.

Figure 4A:
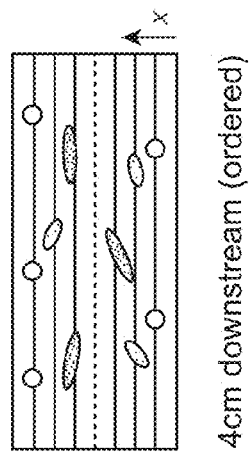
FIG. 4A illustrates a rectangular-shaped channel such as the inertial focusing microchannel with a high-aspect ratio (H>W) in which a random particle distribution is introduced into the inlet.
Figure 4B:
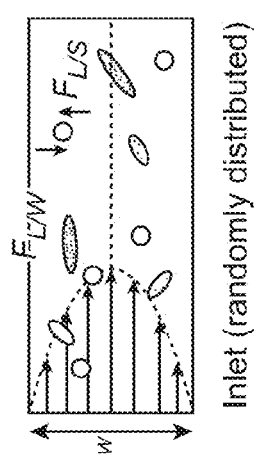
FIG. 4B illustrates a cross-sectional representation of the inertial focusing microchannel 14 at region A of FIG. 1.
Figure 4C:
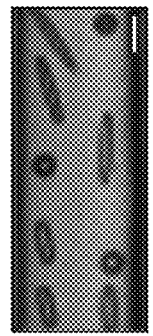
FIG. 4C illustrates a cross-sectional representation of the inertial focusing microchannel 14 at region B of FIG. 1.

FIG. 4A schematically illustrates a rectangular-shaped channel such as the inertial focusing microchannel 14 with a high-aspect ratio (H>W) in which a random particle distribution is introduced into the inlet as shown. At moderate particle Reynolds (Rn) numbers (e.g., those within the range of about 0.3 to about 4) randomly distributed particles are known to focus to two equilibrium regions centered at the faces of the channel. FIG. 4B illustrates a cross-sectional representation of the inertial focusing microchannel 14 at region A of FIG. 1. As seen in FIG. 4B, the various shaped particles are randomly distributed within the fluid. Particles are inertially focused due to the combined effect of $F_{L/W}$ (wall effect) and $F_{L/S}$ (shear gradient). FIG. 4C illustrates a cross-sectional representation of the inertial focusing microchannel 14 at region B of FIG. 1. As seen in FIG. 4C, the different shaped particles reach various equilibrium positions $X_{eq}$ along the width of the inertial focusing microchannel 14. As seen in FIG. 4C, the circular-shaped particles are ordered closer to the walls of the inertial focusing microchannel 14 while the elongated or rod-shaped particles are located in streamlines located closer to the centerline of the inertial focusing microchannel 14. Rod-like particles migrate to a stable position closer to the channel centerline than spherical particles with the same volume, and align such that they periodically "tumble" rotating around a short axis following Jeffery orbits, and are pushed away from the channel wall. Similar to the observations noted above, particles having larger rotational diameters ($D_{max}$) will tend to be collected in streamlines located near the channel centerline (with reference to the inertial focusing microchannel 14) while particles having smaller rotational diameters will tend to be collected in streamlines located laterally away from the channel centerline. Thus, outlets can be selectively positioned laterally with respect to the inertial focusing microchannel 14 to selectively capture sub-populations of particles with different rotational diameters.

Figure 4E:
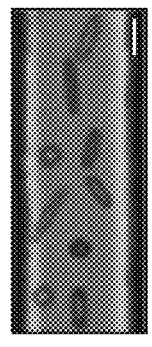
FIG. 4E illustrates a microscopic picture taken of the particles captured at the inlet. The scale bar is 10 μm.
Figure 4F:
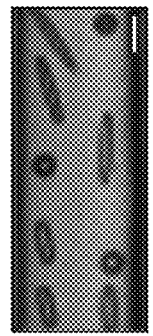
FIG. 4F illustrates a microscopic picture taken of the particles captured at the outlet. The scale bar is 10 μm.
Figure 4D:
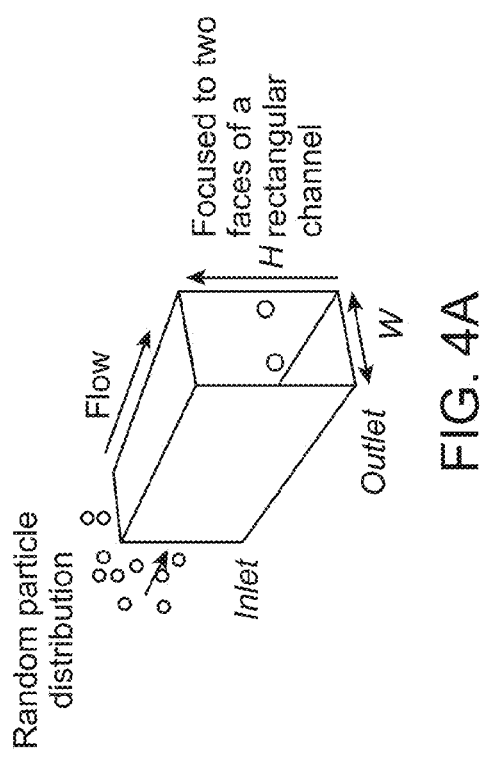
FIG. 4D illustrates the aspect ratios and dimensions of various particles having different sizes and shapes that flow through the particle sorting system. Dimensions are shown in the a and b directions which are generally orthogonal to one another.

FIG. 4D illustrates the aspect ratios and dimensions of various particles having different sizes and shapes that flow through the particle sorting system. FIG. 4E illustrates a microscopic picture taken of the particles captured at the inlet. FIG. 4F illustrates a microscopic picture taken of the particles captured at the outlet. The scale bar in FIGS. 4E and 4F is 10 μm. The various spherical or rod-shaped particles were formed from beads. 3 and 6 μm spherical beads (Polyscience) were stretched to rods with different aspect ratios (R=1:3 and 1:5), following the protocol published previously by Champion et al. See Champion et al., Role of target geometry in phagocytosis, *Proc. Natl. Acad. Sci. USA* 103(13): 4930-4934 (2006). Beads were suspended in 75° C. water—hot-water soluble poly(vinyl alcohol) (PVA)—to a final concentration of 10% wt/vol, 5% wt/vol glycerol, and 0.08% wt/vol spherical polystyrene particles). This solution was spread and dried overnight on a 19×27 cm flat surface. The films were then stretched in mineral oil at 120° C. and dried at room temperature for 20 minutes. To recover the rod-shaped particles, the films were washed with isopropanol and dissolved in 30% isopropanol/water at 75° C. The particles were finally washed eight times, each time with decreasing amounts of isopropanol, in order to remove all PVA from the particle surface. Particle suspensions were injected into tested devices, at a maximum concentration of 1×10⁶ beads/mL, using a syringe pump (Harvard Apparatus PHD 2000) and a glass syringe (Hamilton), at flow rates Q ranging from 20 to 110 μL/min.

The different shaped particles, after being ordered at different equilibrium positions $X_{eq}$, then enter the downstream expanding region 18 which enhances the $X_{eq}$ differences between the particles yet still maintains the particles in respective focused streamlines. The particles are then captured in the various outlet channels 20. As explained above, the resistances of the fluidic resistors 22 can be adjusted to tune the fraction of particles that will be collected from each outlet 20. This is done by tuning the ratio of the fluidic resistances of the outlets 20. This can be expressed by a which represents the ratio of outlet flow rates (Q) from a particular outlet channel ($\alpha_{1:2}=Q_{Outlet\#1}/Q_{Outlet\#2}$), which is directly related to the ratio of outlet fluidic resistances ($\alpha_{1:2}=R_1/R_2$).

In one embodiment of the invention, particles that have run through the particle sorting system 10 and have been collected in the outlets 26 may be run through the particle sorting system 10 one or more additional times to further concentrate or enrich a particle desired particle fraction. For instance, particles may first be run through the particle sorting system at a first flow rate (i.e., Reynolds number) followed by one or more runs through the same device at a different flow rate (i.e., different Reynolds number). In other embodiments, the particles may be run through the particle sorting system 10 only a single time.

Shape represents one of the most important factors to specifically identify a particle. Among other specifications, shape can be a marker of cell cycle status. For example, eukaryotic cells show physical changes in shape which are cell-cycle dependent, such as a yeast cell evoluting from a sphere to a bispherical twin or a larger aggregate, depending on its cell-cycle stage. Shape is also an indicator of cell state and can become an indication used for clinical diagnostics.

For example, blood cell shape may change due to many clinical conditions, diseases and medications, such as the change of red blood cell morphology resulting from parasitic infections (e.g., Sickle cell disease, anemia, malaria). Thus, shape could be used as a specific marker in microfluidic particle separation and may serve as the basis for label-free particle fractionation. Alternatively, different sized particles such as parasites or other pathogens may be removed or extracted from bodily fluids. The ability to continuously focus and separate particles based on their shape has a broad utility for various industrial, clinical and research applications. Even particles having different shapes but similar volumes can be sorted.

Another application of the particle sorting system 10 is the shape-based process of extracting a non-spherical target from a complex sample with spherical objects, such as contaminated water, blood, etc. Cement strength and stability, for instance, are critically linked to particle shape and size. Separation of cement microparticles into pure fractions is hindered by the irregular shapes of the particles that lead to clogging in traditional filters. An approach for filtration of highly defined size particles without clog-prone filters would aid in the development of optimized cement formulations—saving material costs for various construction applications.

The particle sorting system 10 can also be used, to sort particles having different elongation ratios. Elongation of cell shape has also been identified as an indicator of cell cycle, since eukaryotic and prokaryotic cells show physical cycle-dependent changes. Understanding of cell cycles is the subject of many research investigations, which are largely done using yeast cells because of their well-known genetics and their characteristic shape changes during proliferation, e.g., budding yeast cells evolve from a sphere to a bispherical twin or a larger aggregate. Another example are rod-shaped bacteria (e.g., bacilli) that become longer while maintaining the same short dimension depending on the stage of the cell cycle. Enrichment of cells at a certain life-cycle stage can avoid cell-cycle dependent noise, and aid microbiologists in synchronizing a population to better understand population dynamics, environmental effects leading to desynchronization, and stochasticity in single-cell behavior. This synchronization at given cycle-phases is generally done (i) by invasive methods, using chemicals (metabolic agents) which disturb the cell physiology or using a temperature rise, or (ii) by size-based elutriation, which isolates the smaller cells. Invasive methods interfere with the cell metabolism and perturb the natural cycle, while elutriation only provides young cells not yet in active division. The particle sorting system 10 provides a non-invasive, label-free and drug-free continuous method for shape-based yeast cell sorting and synchronization.

More generally, inertial focusing of non-spherical particles is of interest to various research areas. There are many arbitrarily shaped particles widely studied in biology and industrial processing that would be important to focus for counting and analysis purposes. These particles' deviation from the spherical symmetry has been recently demonstrated to result in a considerable increase in the impedance uncertainty, which needs to be considered during the interpretation of electrical measurements of shape. Similarly, in optical measurements of particles based on size, such as scattering measurements, shape can be difficult to ascertain. The precise alignment of shaped particles by inertial focusing, and especially the predictability of their orientation, would help to address this kind of uncertainty and to produce more reliable measurements.

Another application of the particle sorting system 10 is the fluidic alignment of bar-coded particles. Bar-coded particles are fabricated using stop-flow lithography and used for multiplexed and high-throughput biochemical assays. These particles are still limited to few research applications, because of the requirement of their alignment by sheath flow or active guiding rails which complicate their integration in microsystems. Inertial effects can enable precise control of the alignment and focusing of bar-coded particles for the optical reading of their patterns. By eliminating the need for sheath flow, combined with the possibility to work with high flow rates, this can greatly increase the throughput of particle-based bioassays, through high parallelization of the focusing system integrated with a wide-field optical detection.

Another potential application is the sorting of microalgae prior to cytometry, for more effective identification of marine microorganisms in water. Phytoplankton possesses a large variety in shape and size; non-spherical objects rotate and translate vertically in an oscillatory pattern in the channel and depending on their initial angle, cells with the same length may pass through the interrogation region at different angles, causing different scatter signals. The particle sorting system 10 can also be used as an original and passive process of quality control for microparticle fabrication, for example for the selective elimination of aggregates from synthesized particles, based on their aspect ratio.

EXPERIMENTAL

Figure 5A:
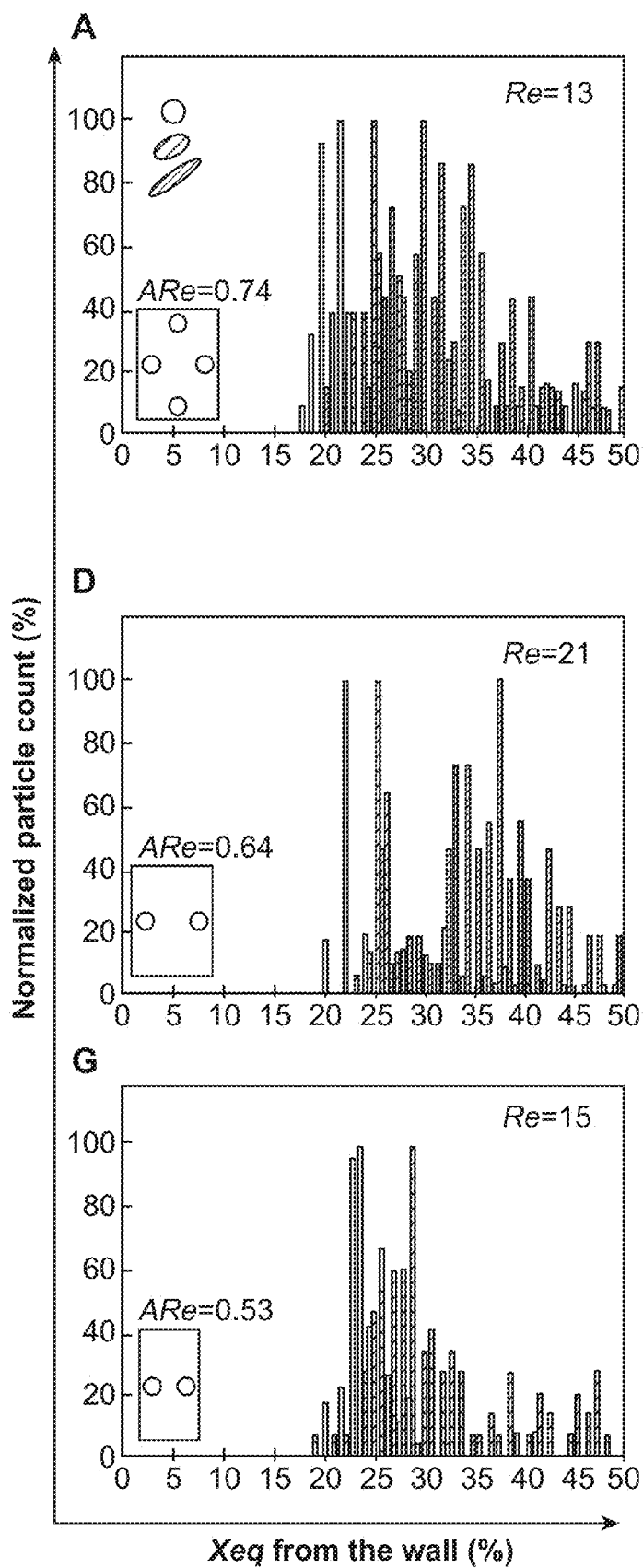
FIG. 5A illustrates histograms plotted to illustrate the variation of distribution for various shaped-particles (spheres, rod with 3:1 aspect ratio, and rod with 5:1 aspect ratio) obtained at different Reynolds numbers (inset) in different channel geometries (illustrated in panel images A, D, and G).
Figure 5A:
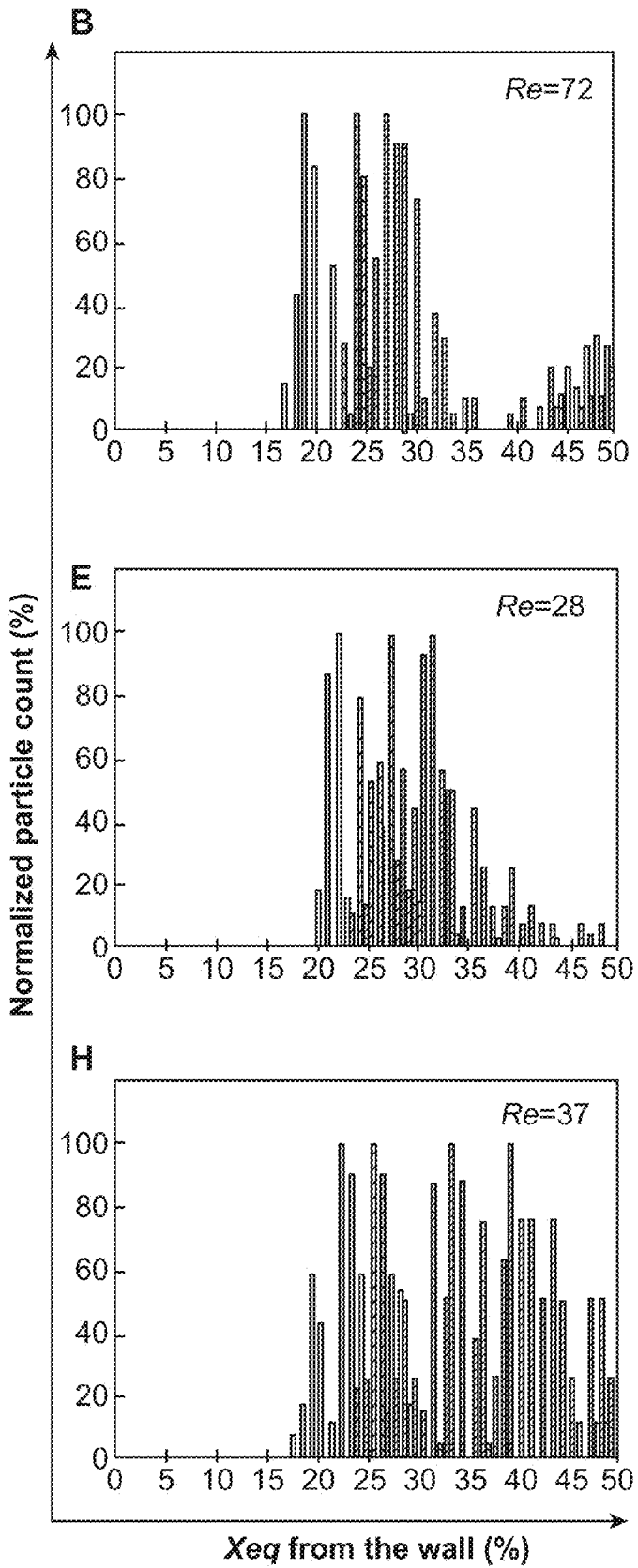

To investigate the effect of shape differences on inertial focusing positions, a systematic study was conducted using a particle sorting system having various channel widths (25, 30 and 35 µm) and a inertial focussing channel of 4 cm in length. A large range of flow rates (20 to 110 µL/min) were tested and $X_{eq}$ was evaluated for each of these conditions. $X_{eq}$ is the particle average equilibrium position, estimated by measuring the distance between the particle center and the channel wall (0% or 50% indicates, respectively, that the particle center is located at the channel wall (0%) or the channel center (50%)), with more than 100 data points for each condition. FIG. 5A illustrates histograms plotted to illustrate the variation of distribution for various shaped-particles (spheres, rod with 3:1 aspect ratio, and rod with 5:1 aspect ratio) obtained at different Reynolds numbers (inset) in different channel geometries. Histogram A of FIG. 5A was prepared from a channel having a width of 35 µm and a flow rate of 20 µL/min. Histogram B of FIG. 5A was prepared from a channel having a width of 35 µm and a flow rate of 110 µL/min. Histogram D of FIG. 5A was prepared from a channel having a width of 30 µm and a flow rate of 30 µL/min. Histogram E of FIG. 5A was prepared from a channel having a width of 30 µm and a flow rate of 40 µL/min. Histogram G of FIG. 5A was prepared from a channel having a width of µm and a flow rate of 20 µL/min. Histogram H of FIG. 5A was prepared from a channel having a width of 25 µm and a flow rate of 50 µL/min.

Figure 5B:
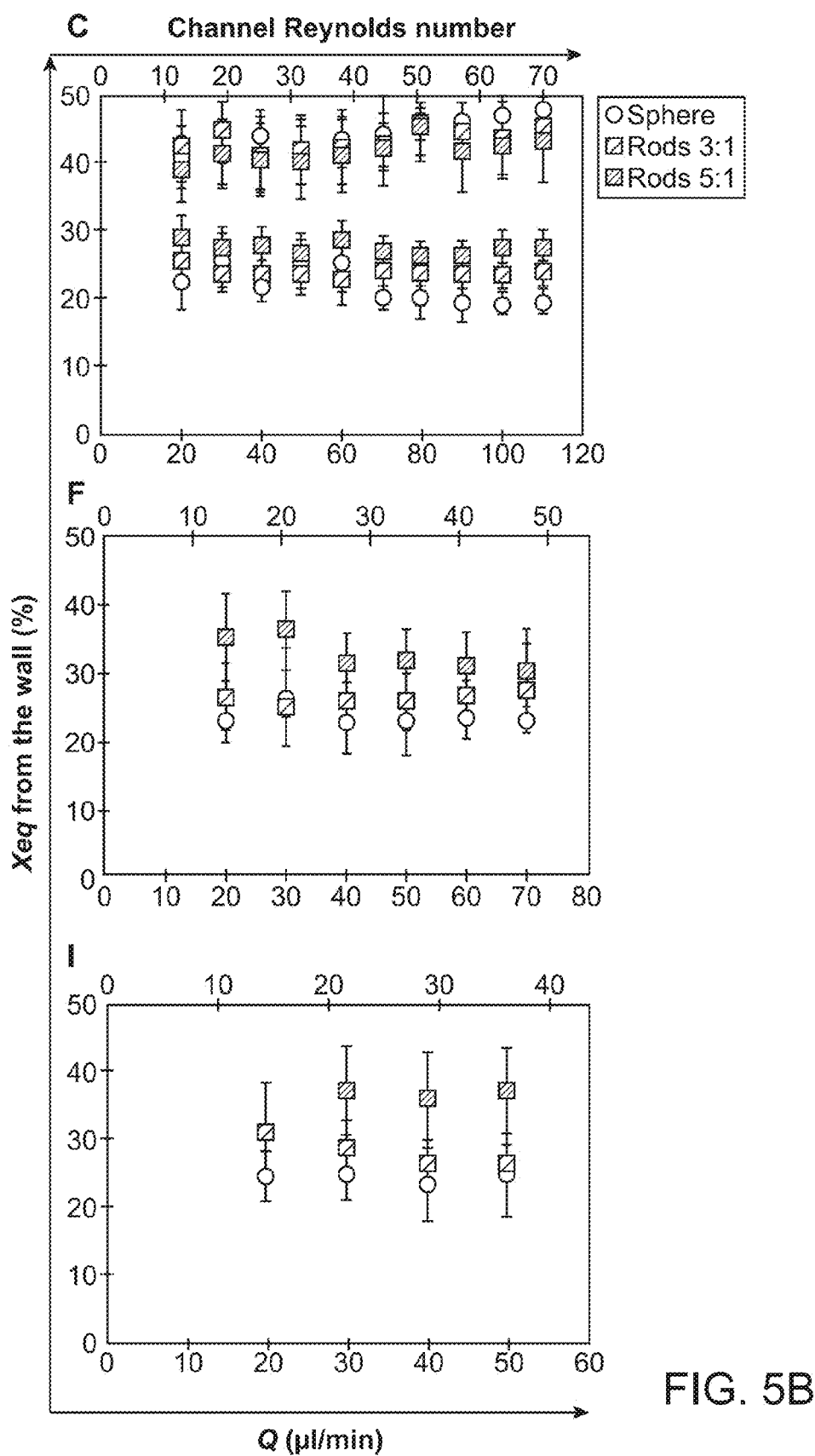
FIG. 5B illustrates the averaged $X_{eq}$ plotted for all three channel geometries and flow conditions tested.

FIG. 5B illustrates the averaged $X_{eq}$ plotted for all three channel geometries and flow conditions tested. Graph C of FIG. 5B was prepared from a device having a channel width of 35 µm. Graph F of FIG. 5B was prepared from a device having a channel width of 30 µm. Graph I of FIG. 5B was prepared from a device having a channel width of 25 µm. Error bars indicate the standard deviation obtained from at least 100 measurements. Flow rate and channel width greatly influence the equilibrium position of the shaped particles.

In the 35 µm wide channel (with a channel aspect ratio closer to 1), at Reynolds numbers higher than 10 (Re=13 or 20

μL/min), inertial effects start to concentrate both spherical and rod-shaped particles. Initially randomly distributed particles with various shapes migrate towards the channel centerline and most importantly, different shaped particles show quite different frequency patterns of particle position. Spheres started to accurately focus and occupy four focusing positions, while rods are more largely spread along the channel width. As the fluid inertia increases further (Re=72 or 110 μL/min), different particle types migrate more distinctly from one another. Spherical particles are the closest to the walls while the distance from either wall increases for higher particle aspect ratios.

Decreasing channel width from 35 to 30 μm changes the aspect ratio of the channel cross-section, which leads to migration to only two (2) distinct equilibrium positions. At 30 μL/min (Re=21) the 1:5 rods were initially separated from spheres and the 1:3 rods. To characterize the possibility of separation, a Separability Factor was defined ($SF_{Type1-Type2}$) which is calculated as the difference in average focusing positions between two kinds of particles, normalized by the average of their standard deviations as shown by Eq. (1) below:

$$SF_{a/b} = \frac{|X_a - X_b|}{\text{mean}(SD_a, SD_b)} \quad (1)$$

FIG. 6A illustrates in panel image A a representative Gaussian fit of normalized particle count (%) as a function of $X_{eq}$ for spherical and 1:5 rod particles. Image B of FIG. 6A illustrates a Gaussian fit of two plots of a Separability Factor of 1. Image C of FIG. 6A illustrates a Gaussian fit of two plots of a Separability Factor of 2. When the channel width was reduced to 30 μm and a flow rate of 30 μL/min (Re=21) the following Separability Factor was measured: $S_{spheres/Rods1:3}$=0.24, $S_{Rods1:3/Rods1:5}$=2.26.

As Q was increased to 40 μL/min (Re=28), both families of rods migrated further away from spheres and from each other, making possible shape-based separation possible; $S_{spheres/Rods1:3}$=0.85, $S_{Rods1:3/Rods1:5}$=1.46. As Re was increased further (Re=49 or 70 μL/min), rods tended to move closer to the walls where spheres are located, reducing the gap between focusing positions; $S_{Spheres/Rods1:3}$=1.05, $S_{Rods1:3/Rods1:5}$=0.61. Decreasing channel width further to 25 μm makes it difficult to focus all particles. Indeed, even at Re=37 (50 μL/min), 1:5 rods are still not focused to a unique streamline. This result is also partly due to the fact that especially with larger rods (5:1 aspect ratio) this narrow channel clogged frequently. These results clearly suggest that optimum conditions exist that maximize the distance between particle positions and allow for the most efficient particle separation. FIG. 6B illustrates the Separability Factor obtained for the 25 μm wide channel (image D), the 30 μm wide channel (image E), and the 35 μm wide channel (image F) at various flow rates.

Shape-based separation experiments were also conducted using the particle sorting system. A mixture of spheres and rods were injected at different flow rates for different outlet designs. The fractions of particles collected from each outlet was analyzed and the separation was characterized using three (3) parameters, defined for a particle type a and an outlet i;

$$EY = \frac{N_a(Outlet_i)}{N_a(\text{inlet})}, \quad EP = \frac{N_a(Outlet_i)}{N_{tot}(Outlet_i)}, \quad (2)$$

$$ER = \frac{N_a(Outlet_i)/N_{tot}(Outlet_i)}{N_a(\text{inlet})/N_{tot}(\text{inlet})}$$

The Extraction Yield (EY) illustrates the outlet repartition of a given particle type, the Extraction Purity (EP) illustrates the particle composition of a given outlet, and the Enrichment Ratio (ER) defines the proportion of particle a in outlet i compared to its proportion at the inlet. FIGS. 7A-7C illustrates three different configurations of a particle sorting system that were tested. The device illustrated in FIG. 7A uses an inertial focusing microchannel that is 25 μm wide having a channel aspect ratio (ARc) of 0.53, with five identical fluidic resistance for each outlet. The flow rate used was 40 μL/min. The device illustrated in FIG. 7B uses an inertial focusing microchannel that has a channel aspect ratio of (ARc=0.64) and a flow rate of 80 μL/min. Five outlets include the following resistances: $\alpha_{1:2}$=¾ and $\alpha_{1:3}$=½. The device illustrated in FIG. 7C uses an inertial focusing microchannel that has a channel aspect ratio of (ARc=0.64) and a flow rate of 70 μL/min. Seven outlets were used including the following resistances: $\alpha_{1:2}$=¾, $\alpha_{1:3}$=½, $\alpha_{1:4}$=¼. The different outlet designs (with differing resistances) in the devices illustrated in FIG. 7A provide a variety of relative capture rations of fluid at the different outlets. By tuning these device parameters we demonstrate a range of possible separations between spheres, 1:3 rods, and 1:5 rods.

FIG. 7D illustrates a micrographic snapshot of the area between outlets 1 and 2 shows that most of spheres and 1:3 rods exit from outlet 1, while 1:5 rods are mostly captured from outlet 2. The ER, EY and EP of different particles at each outlet of the FIG. 7A device are shown below in FIGS. 7G and 7J. FIG. 7E illustrates a micrographic snapshot of the area between outlets 4 and 5. The ER, EY and EP of different particles at each outlet of the FIG. 7B device are shown below in FIGS. 7H and 7K. FIG. 7F illustrates a micrographic snapshot of the area around outlet 5. The ER, EY and EP of different particles at each outlet of the FIG. 7C device are shown below in FIGS. 7I and 7L.

In agreement with SF measurements for these flow conditions ($SF_{Rods1:3/Rods1:5}$=1.9, $SF_{Spheres/Rods1:5}$=2.4 while $SF_{Spheres/Rods1:3}$=0.5), in the FIG. 7A device, 1:5 rods were found to have a high extraction yield in outlets 2 and 4 (86% of 1:5 rods) with up to 90% purity, compared to 1:3 rods and spheres which were mainly collected together in outlets 1 and 5 (83% of all spheres and 70% of all 1:3 rods injected). To achieve another scenario of separation and with a higher flow rate, the experimental conditions were tuned to a channel width aspect ratio of 0.64, and a flow rate of 80 μL/min in the device of FIG. 7B and the ratio of fluidic resistance between the different outlets was modified ($\alpha_{1:2}$=¾, $\alpha_{1:3}$=½). Contrary to before, excellent extraction yield was achieved for spherical particles (85% of all spheres are in outlets 1 and 5), while both types of rods stay together (90% of all rods are extracted in outlets 2 and 4), leading to an extraction purity of 96% for spheres (FIGS. 7H and 7K). These results are still in agreement with SF values, since $SF_{Spheres/Rods1:3}$ increased from 0.5 to 1, while $SF_{Rods1:3/Rods1:5}$ initially at 1.9 decreased to 0.6 for these conditions. Decreasing the flow rate to 60 μL/min in a 30 μm (ARc=0.64) channel using the device illustrated in FIG. 7C allows for separating all three types of particles while slightly decreasing the purity of spheres, as predicted by SF measurements ($SF_{spheres/Rods1:3}$ remains at 1, but $SF_{Rods1:3/Rods1:5}$ increases from 0.6 to 1.3). The presence of seven (7) outlets in this device provides a more accurate separation between streamlines ($\alpha_{1:2}=\frac{3}{4}$, $\alpha_{1:3}=\frac{1}{2}$, $\alpha_{1:4}=\frac{1}{4}$). Indeed, 88% of spheres were isolated in outlets 2 and 6 with 87% purity, 49% of 1:5 rods in outlet 4 with 78% purity, and more interestingly 77% of 1:3 rods with up to 80% purity (FIGS. 7I and 7L).

Inertial shape-based separation is possible for a large range of particle sizes. The separation of 3 µm spheres and 3 µm derived ellipsoids was confirmed experimentally by applying the same concept as was used for separating 6 µm beads with slightly modified parameters. Using the particle sorting system of FIG. 8A, spheres were collected in outlets 1 and 5 with 90% yield (EY) as seen in FIG. 8B and up to 90% purity (EP) as seen in FIG. 8C. With respect to 3:1 rods, an 81% yield (EY) in outlets 2, 3 and 4 was achieved as seen in FIG. 8B and 97% yield of 5:1 rods in outlets 2, 3 and 4 was achieved with up to 88% purity (EP) as seen in FIG. 8C. FIG. 8D illustrates the Enrichment Ratio (ER) for the three shapes. For inertially focusing of particles smaller than 2 µm higher flow rates and pressures are required necessitating materials with higher bond strengths, such as Thermoset Polyester (TPE). The possibility of separating 3 µm beads opens a new range of applications in separation of bacteria to synchronize populations at different stages of cell growth, in which for example, rod-like bacteria can up to double their length.

Shape-based separation using inertial effects can also be used for yeast cell sorting and cell cycle synchronization. Understanding of the cell cycle is the subject of current research, which is often explored using yeast cells (*S. cerevisiae*) because of the well-known genetics and characteristic shape changes; budding yeast cells elongate from a sphere to a bispherical twin or a larger aggregate. Using the particle sorting system of FIG. 7C (ARc=0.64, seven outlets with $\alpha_{1:2}=\frac{3}{4}$, $\alpha_{1:3}=\frac{1}{2}$, $\alpha_{1:4}=\frac{1}{4}$), yeast sorting was conducted at a flow rate of 60 µL/min. Yeast was cultured in Tryptic Soy Broth (TSB) in an incubated shaker (37° C.) for one day prior to the separation experiment. The cultured suspension was diluted in PBS at a non-limiting concentration of $1.5 \times 10^6$ cells/mL and then, similarly to beads, was injected at various flow rates using a Harvard Apparatus syringe pump and Hamilton glass syringe. The separation behavior was captured through high-speed imaging, with the content of each outlet being analyzed by immediate counting with a hemocytometer (Quick-Read). The morphologies of yeast cells were observed and categorized, depending on their cycle state, into (i) small non-dividing singles, (ii) large singles, (iii) budded yeast, (iv) doublets, and (v) aggregates which are composed of three cells or more.

Figure 9A:
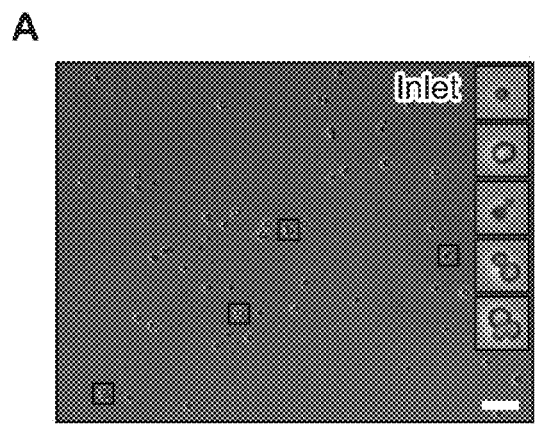
FIG. 9A illustrates a microscopic image of the cells at the inlet of a particle sorting system. Cells are categorized into five groups: small single (top inset), large single (second from top inset), budded (third from top inset), doublet (fourth from top inset) and aggregate (last inset).
Figure 9B:
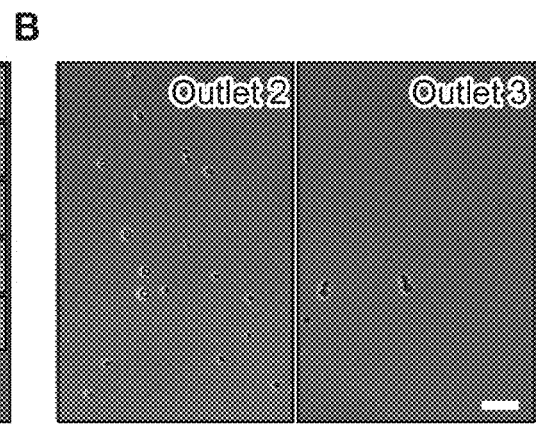
FIG. 9B illustrates respective images of outlet 2 and outlet 3. Singles had a high extraction yield in outlet 2, while in outlet 3 the purity of budded cells increased.

FIG. 9A illustrates a microscopic image of the cells at the inlet of the device. Cells are categorized into five groups: small single (top inset), large single (second from top inset), budded (third from top inset), doublet (fourth from top inset) and aggregate (last inset). FIG. 9B illustrates respective images of outlet 2 and outlet 3. Singles had a high extraction yield in outlet 2, while in outlet 3 the purity of budded cells increased.

Figure 9C:
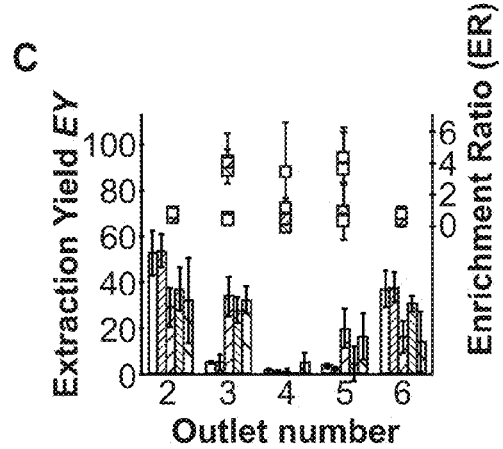
FIG. 9C illustrates a graph of EY and ER for each of the six outlets.
Figure 9D:
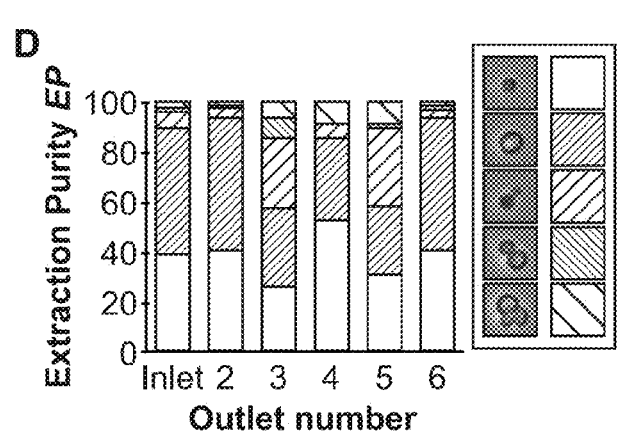
FIG. 9D illustrates a graph of EP for each of the six outlets.

Non-dividing singles were found to have a high extraction yield in outlets 2 and 6 (90% of small singles and 91% of large singles are recovered in these outlets as seen in FIG. 9C), with up to 94% purity (FIG. 9D), while budded yeast cells were mainly collected in outlets 3 and 5 (54% of budded yeast, with up to 31% of purity, compared to 6.6% of purity at the inlet). The higher throughput of the particle sorting system (60 µL/min, i.e., 1500 cells/sec compared to 100 cells/sec) could be further increased by parallelization of the focusing channels, while the purity and enrichment especially needed for this synchronization application improves with cascading several devices in series.

In the experiments it was found that a particle sorting system with ARc=0.53 (W=25 µm, H=47 µm) at Q=40 µL/min that has five (5) outlets with equal resistances to be the best device to separate 6 µm long rods (1:5) from spheres and short rods (1:3), while separating 6 µm spheres from the two kind of rods was best done using ARc=0.64 (W=30 µm, H=47 µm) at Q=80 µL/min with five (5) outlets with $\alpha_{1:2}=\frac{3}{4}$ and $\alpha_{1:3}=\frac{1}{2}$. The best device for separating all three kind of 6 µm particles was ARc=0.64 (W=30 µm, H=47 µm), at Q=70 µL/min with seven (7) outlets with $\alpha_{1:2}=\frac{3}{4}$, $\alpha_{1:3}=\frac{1}{2}$, $\alpha_{1:4}=\frac{1}{4}$. For 3 µm particles spheres could best be separated from the two kinds of rods with ARc=0.53 (W=25 µm, H=47 µm) device at Q=80 µL/min with five (5) outlets with $\alpha_{1:2}=\frac{3}{4}$ and $\alpha_{1:3}=\frac{1}{2}$. Enrichment of budded yeast from the total cell population was successful using a device with ARc=0.64 (W=30 µm, H=47 µm) with seven (7) outlets with $\alpha_{1:2}=\frac{3}{4}$, $\alpha_{1:3}=\frac{1}{2}$, $\alpha_{1:4}=\frac{1}{4}$. Conditions can be optimized for other desired separation modes such as enrichment of singles, etc.

While embodiments of the present invention have been shown and described, various modifications may be made without departing from the scope of the present invention. The invention, therefore, should not be limited, except to the following claims, and their equivalents.

What is claimed is:

1. A particle sorting system, comprising:
   an inlet;
   an inertial focusing microchannel disposed in a substrate and having a downstream expanding region with an increased cross-sectional area at a distal end, wherein the inlet is connected to an upstream end of the microchannel, wherein the inertial focusing microchannel and the downstream expanding region define flow paths uninterrupted by obstacles;
   a source of different shaped particles connected to the inlet, wherein the source of different shaped particles are configured for continuous introduction into the inlet;
   a plurality of outlets connected to the microchannel at the downstream expanding region, with the plurality of outlets located at different lateral positions at the downstream expanding region; and
   a pressure controller connected to the plurality of outlets via fluid lines, wherein the pressure controller applies variable pressures to adjust the respective fluid resistance at the plurality of outlets.

2. The system of claim 1, wherein the particles comprise cells.

3. The system of claim 1, wherein the flow rate of the source of different shaped particles is adjustable.

4. The system of claim 1, wherein the downstream expanding region comprises opposing walls that are progressively angled outward in the direction of fluid flow.

5. The system of claim 4, wherein the opposing walls progressively angle outward at an angle of 2° per 100 µm of movement in the direction of fluid flow.

6. A method of sorting different shaped particles suspended in a sample fluid, comprising:
   flowing the sample fluid containing different shaped particles suspended therein through a particle sorting system at a flow rate between 20 µL/min and 110 µL/min, comprising:
   a single inertial focusing microchannel disposed in a substrate and having a downstream expanding region with an increased cross-sectional area at a distal end, wherein the inertial focusing microchannel and the downstream expanding region define flow paths uninterrupted by obstacles, a plurality of outlets coupled to the downstream expanding region with the plurality of outlets located at different lateral positions at the downstream expanding region, and a plurality of fluidic resistors with each resistor connected to a respective outlet, wherein the plurality of fluidic resistors have different resistances; and collecting fluid in each of the plurality of outlets, wherein at least one of the outlets contains fluid enriched in at least one shape of particle compared to the sample fluid.

7. The method of claim 6, wherein the particles comprise cells.

8. The method of claim 6, wherein the flow rate of the sample fluid is variable.

9. The method of claim 6, wherein the fluidic resistance of the plurality of fluidic resistors is adjustable.

10. The method of claim 9, wherein the fluidic resistance is adjustable via pressure.

11. The method of claim 6, wherein the fluid enriched in at least one shape of particle contains particles having a first shape and fluid in another of the outlets contains particles of a second, different shape wherein the particles of the first shape in the enriched fluid have substantially the same volume as the particles having the second, different shape.

12. The method of claim 6, wherein the fluid enriched in at least one shape of particle contains particles having a first cross-sectional profile and fluid in another of the outlets contains particles of a second, different cross-sectional profile wherein the particles of the first cross-sectional profile in the enriched fluid have a similar cross-sectional profile in one dimension as the particles of the second, different cross-sectional profile but a different cross-sectional profile in another dimension.

13. The method of claim 6, comprising flowing the sample fluid containing different shaped particles suspended therein through the particle sorting system at a first Reynolds number, collecting a sample fluid at one or more of the outlets and reintroducing the collected sample back into the particle sorting system at a second Reynolds number different from the first Reynolds number.

14. The method of claim 6, wherein the plurality of outlets include at least one outlet located at or adjacent to the centerline of the inertial focusing microchannel and at least one outlet located laterally disposed away from the centerline of the inertial focusing microchannel, and wherein the at least one outlet located at or adjacent to a centerline of the inertial focusing microchannel captures a sub-set of particles having larger rotational diameter than another sub-set of particles having a smaller rotational diameter that are collected in the at least one outlet located laterally disposed away from the centerline of the inertial focusing microchannel.

* * * * *